United States Patent [19]

Bach et al.

[11] 4,075,212

[45] Feb. 21, 1978

[54] METHOD OF PREPARING 8,8-DISUBSTITUTED-6-METHYLERGO-LINES AND RELATED COMPOUNDS

[75] Inventors: Nicholas J. Bach; Edmund C. Kornfeld, both of Indianapolis, Ind.

[73] Assignee: Eli Lilly and Company, Indianapolis, Ind.

[21] Appl. No.: 650,582

[22] Filed: Jan. 19, 1976

Related U.S. Application Data

[63] Continuation-in-part of Ser. No. 530,320, Dec. 6, 1974, Pat. No. 3,968,111.

[51] Int. Cl.² .......................................... C07D 457/04
[52] U.S. Cl. .................................. 260/285.5; 424/261
[58] Field of Search ...................................... 260/285.5

[56] References Cited

U.S. PATENT DOCUMENTS

| 2,861,074 | 11/1958 | Kornfeld et al. | 260/285.5 |
| 3,113,133 | 12/1963 | Hofmann et al. | 260/285.5 |
| 3,968,111 | 7/1976 | Bach et al. | 260/285.5 |
| 3,968,112 | 7/1976 | Kornfeld et al. | 260/285.5 |

Primary Examiner—Donald G. Daus
Assistant Examiner—Mary Vaughn
Attorney, Agent, or Firm—James L. Rowe; Everet F. Smith

[57] ABSTRACT

8,8-Disubstituted-6-methylergolines and 9-ergolenes, are prepared by alkylation of lysergic, or isolysergic acid or their 9,10-dihydro analogues.

1 Claim, No Drawings

METHOD OF PREPARING 8,8-DISUBSTITUTED-6-METHYLERGOLINES AND RELATED COMPOUNDS

CROSS REFERENCE

This application is a continuation-in-part of our copending application Ser. No. 530,320, filed Dec. 6, 1974, now U.S. Pat. No. 3,968,111.

BACKGROUND OF THE INVENTION

Compounds based on the ergoline ring system

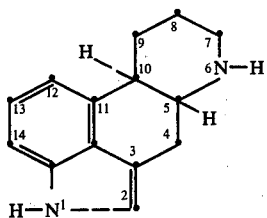

have a surprising variety of pharmaceutical activities. For example, lysergic and isolysergic acid are 8-carboxy-6-methyl-9-ergolenes. The amides of lysergic acid, many of which have valuable and unique pharmacologic properties, include the naturally occurring oxytocic alkaloids-ergocornine, ergokryptine, ergonovine, ergocristine, ergosine, ergotamine, etc. - and synthetic oxytocics such as methergine, as well as the synthetic hallucinogen - lysergic acid diethylamide or LSD. The corresponding amides of 6-methyl-8-carboxyergoline, known generically as dihydroergot alkaloids, are oxytocic agents of lower potency and also lower toxicity than the ergot alkaloids themselves. Recently, it has been found by Clemens, Semonsky, Meites and their various co-workers, that many ergot-related drugs have activity as prolactin inhibitors, including ergocornine, dihydroergocornine, 2-bromo-α-ergokryptine and d-6-methyl-8-cyanomethylergoline. References embodying some of these newer findings in this field of ergoline pharmacology are the following: Naqasawa and Meites, *Proc. Soc. Exp't'l. Biol. Med*, 135, 469 (1970); Lutterbeck et al., *Brit. Med. J.*, 228, (July 24, 1971); Heuson et al., *Europ. J. Cancer*, 353 (1970); *Coll. Czech. Chem. Commun.*, 33 577 (1968); *Nature*, 221, 666 (1969); Seda et al., *J. Reprod. Fert.*, 24, 263 (1971); Mantle and Finn, id 441; Semonsky and co-workers, *Coll. Czech. Chem. Comm*, 36, 2200 (1971); Schaar and Clemens, *Endocr.*, 90, 285-8 (1972); Clemens and Schaar, *Proc. Soc. Exp. Biol. Med.*, 139 659-662-(1972) and Sweeney Clemens, Kornfield and Poore, 64th Annual Meeting, American Association Cancer Research, April 1973. Recently issued patents in the field of ergoline derivatives or lysergic acid derivatives include but are not limited to the following: U.S. Pat. No. 3,704,233, U.S. Pat. No. 3,901,891, U.S. Pat. No. 3,709,891, U.S. Pat. No. 3,585,201, U.S. Pat. No. 3,666,762, U.S. Pat. No. 3,901,893, U.S. Pat. No. 3,752,814, U.S. Pat. No. 3,879,554, U.S. Pat. No. 3,586,683, U.S. Pat. No. 3,717,640, U.S. Pat. No. 3,592,816, U.S. Pat. No. 3,883,655, U.S. Pat. No. 3,901,894, U.S. Pat. No. 3,920,664, U.S. Pat. No. 3,901,894 and U.S. Pat. No. 3,922,347.

Only a few 8,8-disubstituted ergolines have been prepared. A majority of these compounds have also had substituent on the indole nitrogen thus yielding a 1,8,8-trisubstituted derivative. For example, Baker et al. publishing in *Molecular Pharmacology*, 9, 23 (1973) reported 1,8-dimethyl-D-lysergic acid p-bromanilide. This compound showed no hallucinogenic activity unlike D-lysergic acid p-bromanilide. The same compound is mentioned in *Science*, 178, 614 (1972). Troxler and Hofmann *Helvetica Chemica Acta*, 40, 1722 (1957) prepared a mixture of the 1,8-dimethyl and the 8-methyl derivatives of D-isolysergic acid diethylamide. The two products were separated by chromatography. The authors stated, however, that they were unable to obtain similar substitution products alkylated at $C_8$ from dihydrolysergic acid methyl ester although they employed the alkylating mixture which had been used successfully with lysergic acid itself; to wit, 2 moles of methyliodide and 8 moles of potassium amide. These authors also prepared in similar fashion 8-ethyl-D-isolysergic acid diethylamide and the 1,8-dimethyl-D-isolysergic acid diethylamide as a mixture separable by chromatography.

There is no mention in the literature of an 8,8-disubstituted-9-ergolene in which the substituents at 8 are other than amide groups and in which the 1-position is not substituted. 6-Methyl-8,8-disubstituted ergolines are not mentioned in the literature.

SUMMARY OF THE INVENTION

This invention provides a method of preparing compounds of the formula

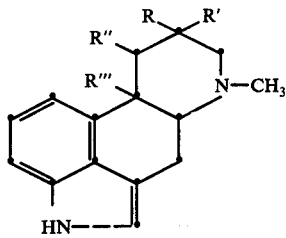

wherein R is alk, carbo($C_1$–$C_3$)alkoxy, Cl or Br;
R' is carboxyl, carbo($C_1$–$C_3$)alkoxy, or $CH_2Z$, wherein alk is ($C_1$–$C_3$)alkyl and
Z is H, OH, CN, $OSO_2$alk, Y-phenyl, or Y-alk, wherein Y is S or O; and
R" and R'" when taken singly are H; and, when taken together with the carbon atoms to which they are attached, form a double bond.

Also included within the scope of the above formula are pharmaceutically-acceptable acid addition salts of the bases represented thereby formed with a non-toxic acid. These pharmaceutically-acceptable salts include salts derived from inorganic acids such as: hydrochloric acid, nitric acid, phosphoric acid, sulfuric acid, hydrobromic acid, hydriodic acid, nitrous acid, phosphorous acid and the like, as well as salts derived from non-toxic organic acids such as aliphatic mono and dicarboxylic acids, phenylsubstituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

In the above formula, the term ($C_1$–$C_3$) alkyl includes the groups methyl, ethyl, propyl, and isopropyl. The term ($C_1$–$C_3$) alkoxy thus includes the terms methoxy, ethoxy, and propoxy and the term carbo ($C_1$–$C_3$) alkoxy includes the terms carbomethoxy, carboethoxy, carbopropoxy and carboisopropoxy. In the above formula, when R' and R'''' are hydrogen, the compound is denominated an ergoline, but when R" and R''', when taken together with the carbon atom to which they are separately attached, form a double bond, the compound is denominated a 9-ergolene. The following compounds exemplify the scope of our invention:

D-6-methyl-8α-ethyl-8β-ethyl-8β-carbomethoxyergoline sulfate

D-6-methyl-8α-isopropyl-8β-chloroergoline phosphate

D-8α-isopropyl lysergic acid

D-8α-ethyl lysergic acid

D-8α-ethyl dihydrolysergic acid

D-8β-methylisolysergic acid

D-6-methyl-8β-ethyl-8α-carbo-n-propoxy-9-ergolene maleate

D-6-methyl-8β-hydroxymethyl-8α-ethyl-9-ergolene succinate

D-6-methyl-8β-cyanomethyl-8α-carboethoxy-9-ergolene

D-6-methyl-8α-cyanomethyl-8β-n-propylergoline hydrochloride

D-6-methyl-8β-mesyloxymethyl-8α-bromoergoline. Tartrate

D-6-methyl-8α-methoxymethyl-8β-carboethoxyergoline citrate

D-6-methyl-8β-ethoxymethyl-8α-carboisopropoxy-9-ergolene lactate

D-6-methyl-8α-phenoxymethyl-8β-carbomethoxyergoline methane sulfonate

D-6-methyl-8β-phenoxymethyl-8α-carboethoxy-9-ergolene

D-8α-phenylmercaptomethyl lysergic acid

D-8α-methylmercaptomethyl lysergic acid toluene sulfonate

D-8β-n-propylmercaptomethyl isolysergic acid, and the like.

The compounds of formula I are white crystalline solids, as are their acid addition salts formed with nontoxic acids. Compounds in which one of R or R' is carbo($C_1$–$C_3$)alkoxy, are prepared by alkylating an ester of lysergic or isolysergic acid or of dihydrolysergic or dihydroisolysergic acid with an alkylating agent of the formula R'''' ($CH_2$)$_n$X wherein R'''' is $CH_3$ CN-$CH_2$ or

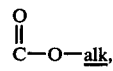

$n$ is 0, 1 or 2 and X is a halogen according to the following reaction scheme:

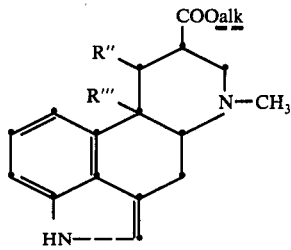

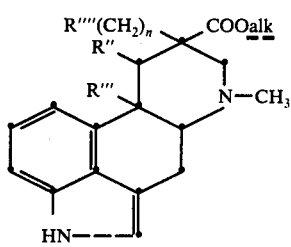

At least two moles of a strong non-hydrolytic base such as sodium amide, potassium amide, lithium tetramethylpiperidide, potassium diisopropyl amide and the like are used to replace both the hydrogens, at $C_8$ and at $C_1$ to form a double anion, which anion then reacts with the alkylating agent, R'''' ($CH_2$)$_n$X. As would be expected, a stronger base is required to react with the $C_8$ hydrogen of II when R" and R''' are H(dihydrolysergic acid) than when R" and R''' form a double bond (lysergic acid) in that the $C_8$ hydrogen in the latter instance is an allylic hydrogen. Thus, bases such as sodium and potassium amide are sufficiently strong to form a 1,8-dianion with lysergic acid, but the stronger bases, lithium tetramethylpiperidide and potassium diisopropylamide, are required to displace the $C_8$ hydrogen of an 8-substituted dihydrolysergic acid. At any rate, at least two moles of a base sufficiently strong to form a 1,8-dianion are required with either lysergic or dihydrolysergic acid. In order to form a $C_8$ alkylation product substantially free from any $C_1$ alkylation product, one mole or less of the alkylating agent is preferably employed. The $C_8$ anion, being more difficult to form than the $C_1$ anion, is more reactive and reacts preferentially with the alkylating agent to form the $C_8$ alkylated product, particularly with regard to the $C_8$ anion from a 9-ergolene, where a large excess of alkylating agent still did not produce $C_1$ alkylation under the standard reaction conditions or Y-alk are prepared in similar fashion by reacting the mesylate ester with phenol or phenylmercaptan, a lower alkanol or a lower alkylmercaptan. Finally, compounds in which R is Cl or Br and R' is carbo ($C_1$–$C_3$)alkoxy are prepared by reacting the alkali metal salt of a lysergic, dihydrolysergic or isolysergic acid corresponding thereto with p-toluenesulfonylchloride, p-toluenesulfonylbromide or other acyl chloride or bromide. In this reaction, surprisingly, the ester group does not replace the anion but the halogen atom.

It will be apparent to those skilled in the art from the above general directions that individual combinations of substituents for R and R' can be achieved by altering the order in which reactions are carried out involving a carbo($C_1$–$C_3$)alkoxy group after the initial reaction with the alkylating agent, R'''' ($CH_2$)$_n$X.

This invention is further illustrated by the following specific examples.

EXAMPLE 1

PREPARATION OF D-6,8-DIMETHYL-8-CARBOMETHOXYERGOLINE

A solution containing 11.5 g. of tetramethylpiperidine in 100 ml. of tetrahydrofuran (THF) was cooled to about −10° C. Fifty ml. of n-butyl lithium as a 1.6 molar solution in hexane was added at such a rate that the temperature remained in the range −10° to −2° C. The resulting mixture was stirred with cooling under a nitrogen atmosphere for about 20 minutes. Next, a solution of 5.7 g. of methyl dihydrolysergate in 125 ml. of THF was added to the reaction mixture at a rate sufficient to keep the temperature in the range −10° to −5° C. The resulting reaction mixture was stirred with cooling under a nitrogen atmosphere for about 15 minutes, after which time a solution of 3.6 g. of methyl iodide in 50 ml. of THF was added rapidly. The temperature rose from −9° C. to about 1° C., and was allowed to continue to rise to 6° C. over a 35 minute period. The reaction mixture was then decomposed by the addition of aqueous acetic acid. The acidic layer was diluted with water and then made basic by the addition of solid sodium bicarbonate. D-6,8-dimethyl-8-carbomethoxyergoline formed in the above reaction was insoluble in the alkaline layer and separated. The separated compound was extracted into chloroform. The chloroform layer was separated and dried, and the chloroform removed by evaporation. Thin layer chromatography of the resulting residue indicated two spots less polar then the methyldihydrolysergate starting material. These spots corresponded to the two isomers, the α-methyl and the β-methyl isomers, produced by the above reaction. The residue was redissolved in chloroform and filtered through 250 g. of florisil to yield a mixture of the two isomers having the structure of D-6,8-dimethyl-8-carbomethoxyergoline. This mixture was chromatographed over 250 g. of florisil, using a chloroform-ether solvent mixture as the eluant, to yield D-6,8β-dimethyl-8α-carbomethoxyergoline melting at about 136°-8° C. in an 18 percent yield and the corresponding 8α-methyl-8β-carbomethoxy isomer melting at about 223°-5° C. with decomposition representing about a 35 percent yield.

Analysis for D-6,8β-dimethyl-8α-carbomethoxyergoline - Calc.: C, 72.46; H, 7.43; N, 9.39; Found: C, 72.29; H, 7.28; N, 9.43.

Analysis for D-6,8α-dimethyl-8β-carbomethoxyergoline - Calc.: C, 72.46; H, 7.43; N, 9.39; Found: C, 72.73; H, 7.69; N, 9.64.

EXAMPLE 2

PREPARATION OF D-6,8β-DIMETHYL-8α-HYDROXYMETHYLERGOLINE

A solution was prepared containing 700 mg. of D-6,8β-dimethyl-8α-carbomethoxyergoline in 100 ml. of THF. 700 mg. of lithium aluminum hydride were added in small portions. The resulting mixture was stirred at ambient temperature under nitrogen atmosphere for about three-quarters of an hour. The reaction mixture was cooled and excess lithium aluminum hydride decomposed by the addition of ethyl acetate. The reaction mixture was then diluted with water and D-6,8β-dimethyl-8α-hydroxymethylergoline formed in the above reaction extracted into chloroform. The chloroform layer was separated and dried. Evaporation of the solvent left as a residue D-6,8β-dimethyl-8α-hydroxymethylergoline which melted at about 219°-221° C. with decomposition after recrystallization from an ether-hexane solvent mixture.

Analysis Calc.: C, 75.52; H, 8.20; N, 10.36; Found: C, 75.46; H, 8.24; N, 10.08.

The above reduction was repeated with D-6,8α-dimethyl-8β-carbomethoxyergoline to prepare D-6,8α-dimethyl-8β-hydroxymethylergoline melting at about 222°-4° C. with decomposition after recrystallization from ethyl acetate.

Analysis Calc.: C, 75.52; H, 8.20; N, 10.36; Found: C, 75.43; H, 8.37; N, 10.11.

EXAMPLE 3

PREPARATION OF D-6,8α-DIMETHYL-8β-MESYLOXYMETHYLERGOLINE

Following the procedure of EXAMPLE 2, 2.1 g. of D-6,8α-dimethyl-8β-carbomethoxyergoline were reduced to the corresponding 8β-hydroxymethyl derivative with lithium aluminum hydride. The crude product of the reaction was dissolved in 50 ml. of pyridine and 0.9 ml. of methanesulfonyl chloride (mesyl chloride) were added in dropwise fashion. The reaction mixture was stoppered, stirred at ambient temperature for about 20 minutes, and was then poured into aqueous sodium bicarbonate. D-6,8α-dimethyl-8β-mesyloxymethylergoline formed in the above reaction was extracted with chloroform. Separation and drying of the chloroform layer followed by evaporation of the chloroform yielded a residue which provided purified D-6,8α-dimethyl-8β-mesyloxymethylergoline melting at 176°-8° C. after recrystallization from ethanol.

Analysis Calc.: C, 62.04; H, 6.94; N, 8.04; Found: C, 61.98; H, 7.10; N, 7.96.

The above reaction was repeated with the D-6,8β-dimethyl-8α-carbomethoxyergoline as a starting material. D-6,8β-dimethyl-8α-mesyloxymethylergoline thus prepared melted at about 160° C. with decomposition after recrystallization from ether.

Analysis Calc.: C, 62.04; H, 6.94; N, 8.04; S, 9.20; found: C, 61.75; H, 7.20; N, 8,31; S, 9.19.

EXAMPLE 4

PREPARATION OF D-6,8β-DIMETHYL-8α-CYANOMETHYLERGOLINE

A reaction mixture was prepared from 200 mg. of D-6,8β-dimethyl-8α-mesyloxymethylergoline, 200 mg. of sodium cyanide in 25 ml. of dimethylsulfoxide (DMSO). The mixture was heated at 100°-120° C. for about 2.25 hours. The reaction mixture was then poured into water and D-6,8β-dimethyl-8α-cyanomethylergoline formed in tha above reaction was extracted with ethyl acetate. The ethyl acetate extract was separated and dried and the ethyl acetate evaporated therefrom. Recrystallization of the resulting residue from ethanol yielded D-6,8β-dimethyl-8α-cyanomethylergoline melting at 250°-5° C. with decomposition.

Analysis Calc.: C, 77.38; H, 7.58; N, 15.04; Found: C, 77.58; H, 7.78; N, 15.12.

Following the above procedure, D-6,8α-dimethyl-8β-mesyloxymethylergoline was reacted with sodium cyanide to yield the corresponding 8β-cyanomethyl compound. The compound was separated from the starting material by chromatography on florisil using chloroform containing 2 percent ethanol as an eluant. D-6,8α-dimethyl-8β-cyanomethylergoline thus prepared melted at 195°–6° C. after recrystallization of material purified by chromatography from a benzene-hexane solvent mixture.

Analysis Calc: C, 77.38; H, 7.58; N, 15.04; Found: C, 77.72; H, 7.57; N, 14.63

EXAMPLE 5

PREPARATION OF D-6,8β-DIMETHYL-8α-PHENYLMERCAPTOMETHLERGOLINE

Following the procedure of Example 4, D-6,8β-dimethyl-8α-mesyloxymethylergoline was reacted with the sodium salt of thiophenol in DMF to yield D-6,8β-dimethyl-8α-phenylmercaptomethylergoline. The reaction mixture was subjected to a 5 percent potassium hydroxide wash to remove any unreacted thiophenol. D-6,8β-dimethyl-8α-phenylmercaptomethylergoline thus formed was purified by chromatography over florisil using chloroform containing 2 percent ethanol as an eluant. Recrystallization of the residue resulting from evaporation of the solvent from chromatographic fractions shown to contain D-6,8β-dimethyl-8α-phenylmercaptomethylergoline by thin layer chromatography yielded purified material melting at 157°–8° C. after recrystallization from ethanol.

Analysis Calc.: C, 76.20; H, 7.23; N, 7.73; S, 8.84; Found: C, 75.99; H, 7.04; N, 7.50; S, 8.99.

The same procedure was carried out on the corresponding 8β-mesyloxy starting material to yield D-6,8α-dimethyl-8β-phenylmercaptomethylergoline which melted at 217°–8° C. with decomposition after recrystallization from ethanol.

Analysis Calc.: C, 76.20; H, 7.23; N, 7.73; Found: C, 76.14; H, 7.39; N, 7.79.

EXAMPLE 6

PREPARATION OF D-6,8,8-TRIMETHYLERGOLINE

About 215 mg. of D-6,8α-dimethyl-8β-phenylmercaptomethylergoline were reacted with about 3 g. of wet Raney nickel in 25 ml. of 95 percent ethanol as a solvent. The reaction mixture was heated to refluxing temperature under a nitrogen atmosphere for about 35 minutes. The mixture was then filtered while hot and the catalyst washed well with 95 percent ethanol. Evaporation of the filtrate yielded D-6,8,8-trimethylergoline as a residue. The compound melted at 221°–2° C. after recrystallization from methanol.

Analysis Calc.: C, 80.27; H, 8.72; N, 11.01; Found: C, 80.33; H, 8.84; N, 11.21.

The procedure was repeated with the corresponding 8α-phenylmercaptomethyl isomer to yield the same D-6,8,8-trimethylergoline having an identical melting point.

EXAMPLE 7

PREPARATION OF D-6-METHYL-8-CARBOMETHOXY-8-CYANOMETHYLERGOLINE

Following the procedure of Example 1, methyl 9,10-dihydrolysergate was alkylated with chloracetonitrile in the presence of tetramethylpiperidine and n-butyl lithium in THF as a solvent to yield a mixture of the 8α-carbomethoxy8β-cyanomethyl and 8α-cyanomethyl-8β-carbomethoxy isomers. The residue containing the isomer mixture prepared by evaporation of the chloroform extract of the work up of the original reaction mixture was subjected to chromatography over florisil using chloroform containing 5 percent ethanol as an eluant. Fractions shown to contain each isomer by thin layer chromatography were combined, the solvent evaporated therefrom and the residue recrystallized. D-6-methyl-8β-cyanomethyl-8α-carbomethoxyergoline was the less polar of the two isomers and was found in the earlier fractions. This isomer melted at 179°–180° C. after recrystallization from an ether-hexane solvent mixture.

Analysis Calc.: C, 70.57; H, 6.55; N, 12.99; Found: C, 70.41; H, 6.55; N, 13.19.

The isomeric D-6-methyl-8α-cyanomethyl-8β-carbomethoxyergoline was more polar than its isomer but less polar than starting material. The compound melted at 220°–3° C. with decomposition after separation by chromatography and recrystallization from an ether-hexane solvent mixture.

Analysis Calc.: C, 70.57; H, 6.55; N, 12.99; Found: C, 70.32; H, 6.79; N, 13.27.

EXAMPLE 8

PREPARATION OF D-6-METHYL-8,8-DICARBOMETHOXYERGOLINE

Following the procedure of Example 1, methyl 9,10-dihydrolysergate was reacted with methylchlorocarbonate in the presence of tetramethylpiperidine and n-butyl lithium in THF solution. D-6-methyl-8,8-dicarbomethoxyergoline formed in the above reaction was isolated as in Example 1 and was purified by chromatography over florisil emloying a 1:1 chloroform-ether solvent mixture as the eluant. Fractions shown to contain D-6-methyl-8,8-dicarbomethoxyergoline by thin layer chromatography were combined, and the residue, obtained by evaporation of the solvent, recrystallized from an ether-hexane solvent mixture to yield crystalline material melting at about 164°–5° C.

Analysis Calc.: C, 66.65; H, 6.48; N, 8.18; Found: C, 66.78; H, 6.51; N, 7.95.

EXAMPLE 9

PREPARATION OF D-6-METHYL-8-CHLOROCARBOMETHOXYERGOLINE

Following the procedure of Example 1, methyl 9,10-dihydrolysergate was reacted with p-toluenesulfonyl chloride in the presence of tetramethylpiperidine and n-butyl lithium in the solution. D-6-methyl-8-chloro8-carbomethoxyergoline formed in the above reaction was isolated by the procedure of Example 1 and was purified by chromatography over florisil using chloroform as the eluant. The major chromatographic fraction from the initial chromatography was less polar than starting material. This fraction was rechromatographed over florisil using chloroform and chloroform ethanol mixtures as the eluant solution. Fractions shown to contain D-6-methyl-8-chloro-8-carbomethoxyergoline by thin layer chromatography were combined and the solvent evaporated therefrom. Recrystallization of the residue from methanol yielded D-6-methyl-8-chloro-8-carbomethoxyergoline melting at 192°–3° C. with decomposition.

Analysis Calc.: C, 64.05; H, 6.01; N, 8.77; Found: C, 64.16; H, 5.72; N, 9.00; Cl, 10.86.

EXAMPLE 10

PREPARATION OF D-2,13-DIBROMO-6,8α-DIMETHYL-8β-CARBOMETHOXYERGOLINE

A solution was prepared containing 825 mg. of D-6,8α-dimethyl-8β-carbomethoxyergoline provided by the procedure of Example 1 in 25 ml. of acetic acid and 15 ml. of chloroform. The solution was cooled to about 0° C. 1.7 g. of pyridine perbromide hydrobromide were added in portions. The reaction mixture was stirred under a nitrogen atmosphere and cooled for about one-half hour and then allowed to warm to room temperature, at which temperature it was stirred for an additional 2.5 hours. The reaction mixture was then poured into aqueous ammonium hydroxide solution. D-2,13-dibromo-6,8α-dimethyl-8β-carbomethoxyergoline formed in the above reaction was extracted with ethyl acetate. The ethyl acetate layer was separated, washed with water and saturated aqueous sodium chloride and then dried. Evaporation of the solvent therefrom yielded a residue which was purified by chromatography using chloroform containing 1 percent ethanol as the eluant. Fractions shown by thin layer chromatography to contain D-2,13-dibromo-6,8α-dimethyl-8β-carbomethoxyergoline were combined and the solvent removed therefrom by evaporation. D-2,13-dibromo-6,8α-dimethyl-8β-carbomethoxyergoline thus prepared melted at 253°-5° C. with decomposition after recrystallization from ether.

Analysis Calc.: C, 47.39; H, 4.42; N, 6.14; Br, 35.03; Found: C, 47.60; H, 4.21; N, 6.11; Br, 34.73.

EXAMPLE 11

PREPARATION OF D-6,8α-DIMETHYL-8β-CARBOMETHOXY-13-BROMOERGOLINE

A solution was prepared containing 450 mg. of D-2,13-dibromo-6,8α-dimethyl-8β-carbomethoxyergoline provided by the procedure of Example 10 in 75 ml. of methanol. About 2 g. of cobalt chloride were added and the suspension cooled to about −20° C. and 1.5 g. of sodium borohydride were added in portions. Stirring was continued at −20 to −30° C. for about one-half hour. The reaction mixture was then diluted with water and D-6,8α-dimethyl-8β-carbomethoxy-13-bromoergoline formed in the reaction extracted with ethyl acetate. The organic layer was separated, washed with water and saturated sodium chloride and then dried. Evaporation of the ethyl acetate therefrom yielded a residue which was purified by filtration through florisil. D-6,8α-dimethyl-8β-carbomethoxy-13-bromoergoline thus prepared was recrystallized from an ether-hexane solvent mixture to yield material melting at 228°-9° C. with decomposition.

Analysis Calc.: C, 57.30; H, 5.61; N, 7.43; Br, 21.18; Found: C, 57.43; H, 5.34; N, 7.57; Br, 20.06 and 20.32.

EXAMPLE 12

PREPARATION OF D-6,8β-DIMETHYL-8α-CARBOMETHOXY-9-ERGOLENE

A solution of 10 g. of diisopropylamine in 150 ml. of THF was prepared and cooled to about −75° C. 60 ml. of an n-butyl lithium solution (about 1.6 M. in hexane) were added slowly thereto. Next, a solution of 7.0 g. of methyl lysergate in 120 ml. of THF was added in dropwise fashion. The resulting precipitate increased the viscosity of the solution, and an additional 120 ml. of THF were added. Next, a solution of 12.4 ml. of methyl iodide in 100 ml. of THF was added rapidly. The temperature rose to about −49° C. during this addition. The reaction mixture was treated with aqueous acetic acid to decompose the organometallics present, and was then diluted with water. The aqueous layer was made basic with dilute aqueous ammonium hydroxide. D-6,8β-dimethyl-8α-carbomethoxy-9-ergolene and its 8α-methyl-8β-carbomethoxy isomer formed in the above reaction, being insoluble in the aqueous alkaline layer, separated and were extracted with ethyl acetate. The ethyl acetate extract was separated, washed with water and then with saturated aqueous sodium chloride. After separation and drying, the volatile constituents of the organic layer were removed by evaporation. A chloroform solution of the resulting residue was filtered through florisil and D-6,8β-dimethyl-8α-carbomethoxy-9-ergolene crystallized therefrom. Recrystallization of D-6,8β-dimethyl-8α-carbomethoxy-9-ergolene from an ether-hexane mixture yielded crystals melting at 117°-19° C.; yield=6.09 g.

Analysis Calc.: C, 72.95; H, 6.80; N, 9.45; Found: C, 73.17; H, 6.89; N, 9.24.

Chromatography over florisil of the residue resulting from evaporation of the mother liquor from the above recrystallization to dryness using chloroform as an eluant, yielded D-6,8β-dimethyl-8α-carbomethoxy-9-ergolene, starting material, and in intermediate fractions, D-6,8α-dimethyl-8β-carbomethoxy-9-ergolene melting at 206°-8° C. with decomposition after recrystallization from ether; yield=78 mg.

Analysis Calc.: C, 72.95; H, 6.80; N, 9.45; Found: C, 72.68; H, 7.05; N, 9.43.

EXAMPLE 13

PREPARATION OF D-6,8β-DIMETHYL-8α-CARBOXY-9-ERGOLENE (α-METHYLISOLYSERGIC ACID)

About 1 g. of D-6,8β-dimethyl-8α-carbomethoxy-9-ergolene as the maleate salt (methyl α-methylisolysergate maleate) was refluxed with about 50 ml. of 10 percent aqueous potassium hydroxide under a nitrogen atmosphere for 3 hours. The reaction mixture was cooled and filtered. The filtrate was made acidic with acetic acid. No precipitate was formed. The filtrate was then made basic with aqueous ammonium hydroxide. No precipitate formed upon addition of the ammonium hydroxide either. The alkaline layer was then extracted with chloroform and the chloroform extract discarded. The alkaline aqueous layer was concentrated to about 50 ml. and filtered. The filter cake was washed with water, ethanol and ether, and dissolved in a small amount of ammonium hydroxide and the resulting solution diluted with water. The resulting alkaline solution was concentrated in vacuo and then diluted to a volume of about 50 ml. with water. The solution was cooled at about 0° C. overnight and the resulting precipitate separated by filtration. The filter cake was again washed with water, ethanol and ether. Drying of the filter cake yielded D-6,8β-dimethyl-8α-carboxy-9-ergolene (α-methylisolysergic acid) melting at 230°-232° C. with decomposition.

Analysis Calc.: C, 72.32; H, 6.43; N, 9.92; Found: C, 72.04; H, 6.22; N, 9.64.

EXAMPLE 14

PREPARATION OF D-6,8β-DIMETHYL-8α-HYDROXYMETHYL-9-ERGOLENE

A solution was prepared containing 4.3 g. of D-6,8β-dimethyl-8α-carbomethoxy-9-ergolene in 100 ml. of THF. 4 g. of lithium aluminum hydride were added in portions while the reaction mixture was cooled in an ice-water bath. An additional 100 ml. of THF were added to decrease the viscosity of the reaction mixture. The reaction mixture was stirred at ambient temperature for about 50 minutes and was then cooled to about 0° C. Excess lithium aluminum hydride and the organometallic salts present were decomposed by the addition of ethyl acetate and water. The reaction mixture was diluted with water and D-6,8β-dimethyl-8α-hydroxymethyl-9-ergolene, formed in the above reaction, extracted into chloroform. The chloroform extract was separated and dried, and the chloroform removed therefrom by evaporation in vacuo. The resulting residue was dissolved in a mixture of chloroform and ether and the solution slurried with 100 g. of florisil. The florisil was separated by filtration to yield a residue comprising D-6,8β-dimethyl-8α-hydroxymethyl-9-ergolene which melted above 100° C. after recrystallization from ether or from ether-hexane. The maleate salt thereof was prepared according to standard procedures and melted at about 200°-2° C. with decomposition after recrystallization from ethanol.

Analysis Calc.: C, 65.61; H, 6.29; N, 7.29; Found: C, 65.56; H, 6.42; N, 7.56.

EXAMPLE 15

PREPARATION OF D-6-METHYL-8-CYANOMETHYL-8-CARBOMETHOXY-9-ERGOLENE

A solution was prepared containing 1.6 g. of diisopropylamine in 20 ml. of THF. The solution was cooled to about −45° C., and 10 ml. of n-butyl lithium solution was added to the diisopropylamine solution at such a rate that the temperature was maintained in the −45 to −35° C. range. The n-butyl lithium was about 1.6 molar in hexane solution. After the addition of the n-butyl lithium was complete, the reaction mixture was stirred and cooled under a nitrogen atmosphere for about 15 minutes. A solution of 1.15 g. of methyl lysergate in 25 ml. of THF was added at a rate such that the temperature of the reaction could be maintained below about −35° C. 10 ml. additional THF were added to decrease the viscosity of the solution. The reaction mixture was cooled and stirred under a nitrogen atmosphere for about 15 minutes. Next, a solution containing 1.2 g. of chloroacetonitrile in 10 ml. of THF was added. The temperature of the reaction mixture was allowed to warm to about 6° C. during a 25 minute period, after which time the reaction mixture was decomposed with aqueous acetic acid. The acidic reaction mixture was diluted with water and was then made basic by the addition of solid sodium bicarbonate. The alkaline layer was extracted with chloroform. D-6-methyl-8-cyanomethyl-8-carbomethoxy-9-ergolene, formed in the above reaction, being insoluble in the alkaline solution, passed into the chloroform layer. The chloroform layer was separated and dried. Evaporation of the chloroform yielded a residue which was chromatographed over florisil using chloroform as the eluant. D-6-methyl-8-cyanomethyl-8-carbomethoxy-9-ergolene was the second component to be eluted. Fractions shown to contain this compound were combined, and the solvent evaporated therefrom. The resulting residue was dissolved in ether, and an ether solution of maleic acid added to form D-6-methyl-8-cyanomethyl-8-carbomethoxy-9-ergolene maleate which melted at 158°-161° C. with decomposition after recrystallization from ethanol. The maleate salt was converted back to the free base and a standard acid-base extraction procedure carried out. Re-extraction of D-6-methyl-8-cyanomethyl-8-carbomethoxy-9-ergolene from the aqueous alkaline layer followed conversion of the resulting residue to the corresponding maleate salt yielded D-6-methyl-8-cyanomethyl-8-carbomethoxy-9-ergolene maleate which melted at 176°-7° C. with decomposition after recrystallization from ether.

Analysis Calc.: C, 63.15; H, 5.30; N, 9.61; Found: C, 63.14; H, 5.05; N, 9.87.

EXAMPLE 16

PREPARATION OF SALTS

Salts of the free bases of this invention, other than the maleate salts whose preparation is illustrated in Examples 14 and 15, are prepared by dissolving the free base in ether and adding an equivalent of a suitable non-toxic acid, also in ether. The salts thus formed, as for example the sulfate and phosphate salts, are insoluble in ether and can be isolated by filtration. Alternatively, the amine base can be dissolved in ethanol and an equivalent of the acid added as an ethanolic solution. In this instance, since the salts thus formed are soluble in the reaction mixture, they are isolated by evaporation of the solvent in vacuo. Salts which can be formed by the above procedure include among others the hydrochloride, sulfate, hydrobromide, phosphate, hydrogen phosphate, dihydrogen phosphate, acetate, maleate, succinate, tartrate, citrate, benzoate, and p-toluene sulfonate salts.

The compounds of this invention are useful as prolactin inhibitors and/or have activity in the central nervous system. The inhibition of prolactin secretion by compounds of this invention is evidenced by the following experiment: Adult male rats of the Sprague-Dawley strain weighing about 200 g. were used. All rats were housed in an air-conditioned room with controlled lighting (lights on 6 a.m. - 8 p.m.) and fed lab chow and water ad libitum.

In each experiment the rats were killed by decapitation, and 150 μl aliquots of serum were assayed for prolactin. Each male rat received an intraperitoneal injection of 2.0 mg. of reserpine in aqueous suspension 18 hours before administration of the ergoline derivative. The purpose of the reserpine was to keep prolactin levels uniformly elevated. The ergoline derivatives under test were dissolved in 10 percent ethanol at a concentration of 10 μg/ml, and were injected intraperitoneally at a standard dose of 50 μg/kg. Each compound was administered to a group of 10 rats, and a control group of 10 intact males received an equivalent amount of 10 percent ethanol. One hour after treatment, all rats were killed by decapitation, and the serum was collected and assayed for prolactin as previously described.

The difference between the prolactin level of the treated rats and prolactin level of the control rats, divided by the prolactin level of the control rats gives the percent inhibition of prolactin secretion attributable to the compounds of this invention. The table which follows gives prolactin inhibition percentages for a series of compounds coming within the scope of Formula I above tested at the 10 μg/rat level. In the table, column 1 gives the name of the compound and column 2, the percent prolactin inhibition.

TABLE

| Name of Compound | % Prolactin Inhibition |
|---|---|
| D-6-methyl-8α-cyanomethyl-8β-carbomethoxyergoline | 57 |
| D-6,8α-dimethyl-8β-mesyloxymethylergoline | 64 |
| D-6,8α-cyanomethyl-6,8β-dimethylergoline | 53 |
| D-6,8α-dimethyl-8β-cyanomethylergoline | 50 |
| D-6,8α-dimethyl-8β-carbomethoxyergoline | 62 |
| D-6,8α-dimethyl-8β-carbomethoxy-9-ergolene | 45 |
| D-2,13-bromo-6,8α-dimethyl-8β-carbomethoxy-ergoline | 39 |

Other compounds provided by this invention have marginal prolactin inhibiting action at the 10 μg/rat level but would have a more significant action at higher levels (100 μg to 1 mg).

As prolactin inhibitors, the compounds are useful in the treatment of inappropriate lactation such as undesired postpartum lactation and galactorrhea. In addition, they can be used to treat prolactin-dependent adenocarcinomas and prolactin-secreting pituitary tumors as well as the following disorders: Forbes - Albright syndrome, Chairi - Frommel syndrome, gynecomastia itself and gynecomastia occurring as a result of estrogenic steroid administration for prostatic hypertrophy, fibrocystic disease of the breast (benign nodules), prophylactic treatment of breast cancer, and breast development resulting from the administration of psychotropic drugs, for example, thorazine, or for prostatic hypertrophy itself.

In using the compounds of this invention to inhibit prolactin secretion, and 8,8-disubstituted-6-methylergoline according to Formula I above, or a salt thereof with a pharmaceutically-acceptable acid is suspended in corn oil and the suspension injected parenterally or fed to a female mammel in amounts varying from 0.01 to 10 mg/kg/day of mammalian weight. Oral administration is preferred. If parenteral administration is used, the injection is preferably by the subcutaneous route using an appropriate pharmaceutical formulation. Other modes of parenteral administration such as intraperitoneal, intramuscular, or intravenous routes are equally effective. In particular, with intravenous or intramuscular administration, a soluble pharmaceutically-acceptable salt of an 8,8-disubstituted-6-methylergoline, preferably the methanesulfonate salt, according to Formula I either as the free base or in the form of a salt thereof can also be mixed with standard pharmaceutical excipients and loaded into empty telescoping gelatin capsules or pressed into tablets.

The compounds also have CNS depressant activity and are therefore useful as general sedatives, etc. For example, D-6-methyl-8α-carbomethoxy-8β-cyanomethyl-9-ergolene maleate, the corresponding-8α-carbomethoxy-8β-methyl compound and the corresponding 8,8-dimethyl derivatives manifest such activity.

We claim:

1. The process which comprises reacting a $(C_1-C_3)$ alkyl dihydrolysergate of the formula

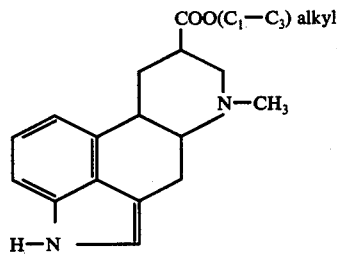

with at least 2 moles of non-hydrolytic base of the class consisting of lithium tetramethylpiperidide and potassium diisopropyl amide in an inert solvent to form a 1,8-dianion of the said $(C_1-C_3)$ alkyl dihydrolysergate, and then reacting said dianion with not more than one mole of an alkylating agent, $R''''(CH_2)_n X$ wherein $R''''$ is $CH_3$, $CH_2$, CN or

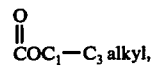

X is halogen and $n$ is 0, 1 or 2 to yield a $(C_1-C_3)$ alkyl 8-$R''''$ dihydrolysergate substantially free from any 1,8-di $R''''$ dihydrolysergate and then isolating the thus formed $(C_1-C_3)$ alkyl 8-$R''''$ dihydrolysergate in substantially pure form from the reaction mixture.

* * * * *

United States Patent and Trademark Office

CERTIFICATE OF CORRECTION

PATENT NO. : 4,075,212
DATED : February 21, 1978
INVENTOR(S) : Nicholas J. Bach, et al.

It is certified that error appears in the above-identified patent and that said Letters Patent are hereby corrected as shown below:

Column 9, line 1, after "N, 8.77;" insert --Cl, 11.12--.

Signed and Sealed this

Sixth Day of February 1979

[SEAL]

Attest:

RUTH C. MASON
Attesting Officer

DONALD W. BANNER
Commissioner of Patents and Trademarks